(12) United States Patent
Matsubara et al.

(10) Patent No.: US 10,065,011 B2
(45) Date of Patent: Sep. 4, 2018

(54) GAS SUPPLY MASK APPARATUS

(71) Applicant: Atom Medical Corporation, Tokyo (JP)

(72) Inventors: Kazuo Matsubara, Tokyo (JP); Terumi Matsubara, Saitama (JP); Kenji Kobayashi, Saitama (JP); Shinichi Kobayashi, Saitama (JP)

(73) Assignee: Atom Medical Corporation, Tokyo (JP)

( * ) Notice: Subject to any disclaimer, the term of this patent is extended or adjusted under 35 U.S.C. 154(b) by 526 days.

(21) Appl. No.: 14/717,180

(22) Filed: May 20, 2015

(65) Prior Publication Data

US 2015/0335844 A1    Nov. 26, 2015

(30) Foreign Application Priority Data

May 21, 2014   (JP) .................................. 2014-105147
May 30, 2014   (JP) .................................. 2014-112844
Jun. 12, 2014   (JP) .................................. 2014-121585

(51) Int. Cl.
*A61M 16/06*    (2006.01)
*A61M 16/08*    (2006.01)

(52) U.S. Cl.
CPC ........ *A61M 16/0683* (2013.01); *A61M 16/06* (2013.01); *A61M 16/0816* (2013.01); *A61M 2202/0208* (2013.01)

(58) Field of Classification Search
CPC .............. A61M 16/0683; A61M 16/06; A61M 16/0816; A61M 2202/0208

(Continued)

(56) References Cited

U.S. PATENT DOCUMENTS 2,248,477 A    7/1941   Lombard
2,535,938 A    12/1950  Lombard (Continued)

FOREIGN PATENT DOCUMENTS

JP    S34-9100 B    10/1959
JP    S6318154 U    2/1988

(Continued)

OTHER PUBLICATIONS

Office Action issued in JP Application No. 2014-105147 dated April 20, 2017.

(Continued)

*Primary Examiner* — Andrew S Lo
(74) *Attorney, Agent, or Firm* — Hunton Andrews Kurth LLP

(57) ABSTRACT

A gas supply mask apparatus allows a mask wearer to inhale a gas such as oxygen gas such that air in a mask main body does not much mix in the gas approaching substantially lower ends and the vicinities of the nostrils of the mask wearer in the mask main body. In this gas supply mask apparatus, a gas introduction opening for introducing a gas such as oxygen gas and water vapor into the mask main body includes a first gas introduction opening capable of introducing the gas in, e.g., a bundle-like state into the mask main body, and a second gas introduction opening capable of introducing the second gas into the mask main body so as to surround, in a substantially ring-like state, the above-mentioned, first gas in a bundle-like state introduced into the mask main body from the first gas introduction opening.

29 Claims, 11 Drawing Sheets

(58) Field of Classification Search
USPC .................................................. 128/206.21
See application file for complete search history.

(56) References Cited

U.S. PATENT DOCUMENTS

| | | | |
|---|---|---|---|
| 2,928,387 A | 3/1960 | Layne | |
| 3,042,035 A | 7/1962 | George | |
| 3,680,555 A | 8/1972 | Warncke | |
| 3,850,171 A | 11/1974 | Ball et al. | |
| 4,201,205 A | 5/1980 | Bartholomew | |
| 4,279,037 A | 7/1981 | Morgan | |
| 4,794,921 A * | 1/1989 | Lindkvist | A61M 16/06 128/203.29 |
| 4,875,477 A | 10/1989 | Waschke et al. | |
| 5,005,571 A | 4/1991 | Dietz | |
| 5,441,046 A | 8/1995 | Starr et al. | |
| 5,465,712 A * | 11/1995 | Malis | A61M 16/06 128/203.11 |
| 5,483,953 A * | 1/1996 | Cooper | A61M 11/06 128/200.14 |
| 5,724,965 A | 3/1998 | Handke et al. | |
| 5,738,094 A | 4/1998 | Hoftman | |
| 6,035,852 A | 3/2000 | Hoftman | |
| 6,491,034 B1 | 12/2002 | Gunaratnam et al. | |
| 6,675,796 B2 * | 1/2004 | McDonald | A61M 16/06 128/200.28 |
| 7,926,487 B2 | 4/2011 | Drew et al. | |
| 8,042,540 B2 | 10/2011 | McDonald | |
| 8,646,449 B2 | 2/2014 | Bowsher | |
| 8,733,356 B1 | 5/2014 | Roth | |
| 9,010,330 B2 | 4/2015 | Barlow et al. | |
| 9,144,656 B2 | 9/2015 | Lang et al. | |
| 9,186,474 B1 | 11/2015 | Rollins | |
| 9,272,108 B2 | 3/2016 | Hu | |
| 2003/0154984 A1 | 8/2003 | Fernandes | |
| 2004/0045550 A1 | 3/2004 | Lang et al. | |
| 2004/0112385 A1 * | 6/2004 | Drew | A61M 16/06 128/206.21 |
| 2006/0048774 A1 | 3/2006 | Townsend | |
| 2006/0081248 A1 | 4/2006 | McDonald | |
| 2006/0102185 A1 | 5/2006 | Drew et al. | |
| 2006/0196510 A1 * | 9/2006 | McDonald | A61M 16/06 128/206.21 |
| 2007/0125379 A1 * | 6/2007 | Pierro | A61M 16/0666 128/204.23 |
| 2008/0149105 A1 | 6/2008 | Matula et al. | |
| 2009/0050156 A1 * | 2/2009 | Ng | A61M 16/06 128/205.24 |
| 2009/0250061 A1 | 10/2009 | Marasigan | |
| 2009/0260628 A1 | 10/2009 | Flynn | |
| 2010/0122705 A1 | 5/2010 | Moenning | |
| 2010/0236549 A1 | 9/2010 | Selvarajan et al. | |
| 2010/0258133 A1 | 10/2010 | Todd et al. | |
| 2011/0180078 A1 | 1/2011 | McKinley | |
| 2011/0155140 A1 | 6/2011 | Ho et al. | |
| 2011/0197341 A1 | 8/2011 | Formica et al. | |
| 2012/0042878 A1 | 2/2012 | Woo | |
| 2012/0055485 A1 | 3/2012 | Anthony | |
| 2012/0204872 A1 * | 8/2012 | Cohen | A61M 16/0666 128/203.12 |
| 2012/0222678 A1 | 9/2012 | Colbaugh | |
| 2012/0318271 A1 | 12/2012 | Ho | |
| 2012/0318274 A1 | 12/2012 | Ho | |
| 2013/0192601 A1 * | 8/2013 | Reischl | A61M 16/06 128/205.25 |
| 2014/0090649 A1 | 4/2014 | Groll et al. | |
| 2014/0107517 A1 | 4/2014 | Hussain | |
| 2014/0150798 A1 | 6/2014 | Fong et al. | |
| 2014/0305433 A1 | 10/2014 | Rothermel | |
| 2014/0305436 A1 * | 10/2014 | Nitta | A61M 15/0085 128/204.25 |
| 2015/0107568 A1 | 4/2015 | Kuo | |
| 2015/0297854 A1 | 10/2015 | McCracken | |
| 2015/0328423 A1 | 11/2015 | Siew et al. | |
| 2016/0008558 A1 * | 1/2016 | Huddart | A61M 16/06 128/205.25 |
| 2016/0184549 A1 | 6/2016 | Bugamelli et al. | |
| 2016/0310688 A1 | 10/2016 | Rothermel | |

FOREIGN PATENT DOCUMENTS

| | | |
|---|---|---|
| JP | 2005-253925 | 9/2005 |
| WO | 2013144753 A1 | 10/2013 |

OTHER PUBLICATIONS

Office Action issued in JP Application No. 2014-121535 dated May 10, 2017.
Office Action issued in JP Application No. 2014-112844 dated May 12, 2017.
Non-final Office Action dated Sep. 28, 2017, in U.S. Appl. No. 14/717,163.
Non-final Office Action dated Sep. 27, 2017, in U.S. Appl. No. 14/717,173.
Office Action issued in JP Application No. 2014-105147 dated Apr. 20, 2017.
Office Action issued in JP Application No. 2014-121585 dated May 10, 2017.

* cited by examiner

GAS SUPPLY MASK APPARATUS

CROSS-REFERENCE TO RELATED APPLICATIONS

This patent application claims priority to Japan Patent Application No. 2014-105147, filed May 21, 2014, and Japan Patent Application No. 2014-112844, filed May 30, 2014, and Japan Patent Application No. 2014-121585, filed Jun. 12, 2014, the disclosures of each of which are herein incorporated by reference in their entirety.

TECHNICAL FIELD

The present invention relates to a gas supply mask apparatus such as an oxygen mask apparatus comprising a mask main body wearable on a head of a mask wearer, and a gas introduction opening capable of introducing a gas such as oxygen gas and water vapor to a gas introduction space existing between a face of the mask wearer and the mask main body.

BACKGROUND OF THE INVENTION

In FIG. 10, a conventional oxygen mask is shown. A conventional oxygen mask apparatus 101 shown in FIG. 10 differs from an oxygen mask apparatus 1 according to an embodiment of the present invention shown in FIGS. 1 to 8 in points to be described below. That is, in the conventional oxygen mask apparatus 101, a first connector 102 is attached to a mask main body 103 such that the axis of the first connector 102 extends in a substantially vertical direction. In addition, a second connector 104 is formed into a substantially cylindrical shape so that the axis of the second connector 104 extends in a substantially vertical direction. Therefore, oxygen gas which rises substantially vertically from a gas supply tube 105 rises substantially vertically in a third connector 106, and is introduced to the second connector 104. Also, this oxygen gas introduced to the second connector 104 rises in the first connector 102. Accordingly, the oxygen gas rises in the mask main body 103 while diffusing from a relatively large upper-end opening 107 of the first connector 102. Therefore, a mask wearer 111 can relatively easily inhale, from the nostrils, the oxygen gas having flowed to a portion, below a nose 112, and the vicinity. Reference numeral 113 denotes three left slit-like holes.

In the conventional oxygen mask apparatus 101 shown in FIG. 10, the upper-end opening 107 of the first connector 102 has substantially the same diameter as that of an inner circumferential hole (in other words, a through hole) 114 of the first connector 102. Accordingly, the oxygen gas flowing into the mask main body 103 from the upper-end opening 107 may evenly spread to a substantially whole interior of the mask main body 103. To allow the mask wearer 111 to properly inhale the oxygen gas from the nostrils, therefore, a relatively large amount of the oxygen gas must be supplied into the mask main body 103. Accordingly, especially when the mask main body 103 is not well fitted on a face 115 of the mask wearer 111, the oxygen gas having risen in the mask main body 103 may flow out from the upper end and the vicinity of the mask main body 103, and flow toward an eye 116 of the mask wearer 111. As a consequence, the eye 116 of the mask wearer 111 may become dry, and the mask wearer 111 may have discomfort on the eye 116. In addition, the three slit-like holes 113 are formed on each of the left and right sides of the conventional oxygen mask apparatus 101.

When the mask wearer 111 exhales a large amount of breath, the internal pressure of the mask main body 103 rises, so the mask wearer 111 becomes uncomfortable. Also, this uncomfortable feeling becomes significant if the volume of air to be breathed in and out increases.

To correct the above-described drawback of the conventional oxygen mask apparatus 101 shown in FIG. 10, an oxygen mask apparatus 121 of a modification shown in FIG. 11 can be formed by deforming the conventional oxygen mask apparatus 101. More specifically, in this oxygen mask apparatus of the modification shown in FIG. 11, left and right large ventilation holes 122, which can substantially be the same as left and right large ventilation holes 22a and 22b shown in, e.g., FIG. 1, are formed instead of the three slit-like holes 113 in the conventional oxygen mask apparatus 101 shown in FIG. 10. In the oxygen mask apparatus 121 of the modification shown in FIG. 11, therefore, the ventilation holes 122 are larger than those of the conventional oxygen mask apparatus 101 shown in FIG. 10, so the uncomfortable feeling of the mask wearer 111 when he or she breathes can be improved. However, a large amount of oxygen gas introduced from the upper-end opening 107 of the first connector 102 to a gas introduction space 123 may flow outside the mask main body 103 from the large holes 122, or a large amount of air may flow into the gas introduction space 123 of the mask main body 103 from outside the mask main body 103 and mix with the oxygen gas. When using the oxygen mask apparatus 121 shown in FIG. 11, therefore, it is relatively difficult to allow the mask wearer 111 to inhale the oxygen gas at an appropriate concentration.

SUMMARY OF THE INVENTION

The present invention can effectively correct the above-described drawbacks of the conventional oxygen mask apparatus 101 and the oxygen mask apparatus 121 of the above-mentioned modification by using a distinct arrangement.

According to the main aspect, the present invention is directed to a gas supply mask apparatus comprising a mask main body wearable on a head of a mask wearer, and a gas introduction opening capable of introducing a gas to a gas introduction space existing between a face of the mask wearer and the mask main body, wherein the gas introduction opening includes a first gas introduction opening capable of introducing the gas to the gas introduction space, and a second gas introduction opening capable of introducing the gas in a substantially ring-like state to the gas introduction space, such that it is possible to substantially surround the gas introduced from the first gas introduction opening to the gas introduction space. In this arrangement, a second gas introduced from the second gas introduction opening to the gas introduction space starts flowing in the gas introduction space while surrounding, in a substantially ring-like state, a substantially outer circumference of a first gas introduced from the first gas introduction opening to the gas introduction space. Therefore, when the mask wearer breathes in, for example, he or she can effectively inhale both the first gas and second gas from the nostrils. When the mask wearer does not breathe in, for example, the gas flow of the second gas surrounds the outer circumference of the first gas in a substantially ring-like state. This makes it possible to effectively prevent the first gas from leaking outside the mask main body from, e.g., the pair of left and right ventilation holes.

According to the first aspect, the present invention has an arrangement in which the first gas introduction opening can introduce the gas in a substantially bundle-like state to the gas introduction space. According to the second aspect, the present invention has an arrangement in which when an introduction direction of the gas to be introduced from the first gas introduction opening to the gas introduction space is a first introduction direction, and an introduction direction of the gas to be introduced from the second gas introduction opening to the gas introduction space is a second introduction direction, an angle which the second introduction direction makes with the first introduction direction falls within a range of 40° to 62° (preferably, a range of 42° to 60°, and more preferably, a range of 44° to 58°). According to the first mode of the third aspect, the present invention has an arrangement in which in a mask placement state in which the mask main body is placed upward on a horizontal surface, a first angle formed between the horizontal surface and a direction in which the first gas introduction opening faces falls within a range of 30° to 60° (preferably, a range of 35° to 55°, and more preferably, a range of 40° to 50°) when the mask main body is viewed sideways (e.g., from the right side of the mask main body), and in the mask placement state, a second angle formed between the direction in which the first gas introduction opening faces and a bisecting central line which bisects the mask main body into left and right halves when the mask main body is viewed from above falls within a range of 0° to 15° (preferably, a range of 0° to 10°, and more preferably, a range of 0° to 5°) when the mask main body is viewed from above. According to the second mode of the third aspect, the present invention has an arrangement in which in a correct mask wearing state in which a mask wearer having an average body shape and an average head shape is correctly wearing the mask main body and facing forward, a third angle formed between a direction in which the first gas introduction opening faces and a virtual vertical plane facing forward falls within a range of 30° to 60° (preferably, a range of 35° to 55°, and more preferably, a range of 40° to 50°) when the mask main body is viewed from the side, and in the correct mask wearing state, a fourth angle formed between the direction in which the first gas introduction opening faces and a bisecting central line which bisects the mask main body into left and right halves when the mask main body is viewed frontways falls within a range of 0° to 15° (preferably, a range of 0° to 10°, and more preferably, a range of 0° to 5°) when the mask main body is viewed frontways. In the arrangement of at least one of the first aspect, the second aspect, and the first and second modes of the third aspect, the effect achieved by the main aspect of the present invention can be achieved further reliably with a relatively simple arrangement and relatively simple operation.

According to the fourth aspect, the present invention comprises a gas supply cylindrical portion extending substantially along a direction in which the first gas introduction opening faces, a gas straightening portion having a substantially inverted frustum shape and formed on an upper-end side of the gas supply cylindrical portion to project from the upper-end side, and a gas outlet formed into a substantially ring-like shape between the gas straightening portion having a substantially inverted frustum shape and the gas supply cylindrical portion. In this arrangement, a gas flow including a substantially central gas which flows while substantially broadening forward in the mask main body, and a substantially ring-like gas which surrounds the substantially central gas or the like, can be formed relatively easily with a relatively simple arrangement and relatively simple operation.

According to the fifth aspect, the present invention comprises a gas supply cylindrical portion configured to supply a gas into the mask main body from outside the mask main body through a gas passing opening and the first gas introduction opening and the second gas introduction opening, wherein the gas supply cylindrical portion comprises a first cylindrical portion configured to transfer the gas substantially upward, and a second cylindrical portion connected to an upper portion of the first cylindrical portion, and the second cylindrical portion is configured to supply the gas to the first gas instruction opening and the second gas introduction opening after deflecting a direction of a flow of the gas supplied from the first cylindrical portion to the direction in which the first gas introduction opening faces. In this arrangement, when supplying a gas from the gas supply tube to the gas introduction opening through the gas supply cylindrical portion, the gas supply tube can be suspended substantially downward from the gas supply cylindrical portion. This makes handling of the gas supply tube relatively easy as in the conventional oxygen mask apparatus shown in FIG. 10.

According to the sixth aspect, the present invention comprises a first connector including the first gas introduction opening and the second gas instruction opening, and a second connector connected to the first connector to extend outside the mask main body, wherein the second connector includes a lower cylindrical portion extending substantially downward, and an upper cylindrical portion integrated with the lower cylindrical portion to extend obliquely upward in a bent state from the lower cylindrical portion, and the upper cylindrical portion is configured to be pivotal with respect to the first connector. In this arraignment, the effect achieved by the fifth aspect can be achieved further reliably with a relatively simple structure and relatively simple operation.

According to the first mode of the sixth aspect, the present invention has an arrangement in which the first connector includes a gas supply cylindrical portion extending substantially along a direction in which the first gas introduction opening faces, a gas straightening portion having a substantially inverted frustum shape and formed on an upper-end side of the gas supply cylindrical portion to project from the upper-end side, and a gas outlet formed into a substantially ring-like shape between the gas straightening portion having a substantially inverted frustum shape and the gas supply cylindrical portion. In this arrangement, the effect achieved by the main aspect can be achieved further reliably with a relatively simple and relatively small structure.

According to the second mode of the sixth aspect, the present invention has an arrangement in which a length of the gas supply cylindrical portion in a first direction in which the first gas introduction opening of the first connector faces falls within a range of 6 to 12 mm (preferably, a range of 6.5 to 11.5 mm, and more preferably, a range of 7.2 to 10.8 mm), and an inside area of the first connector in a direction substantially perpendicular to the first direction falls within a range of 118 to 236 $mm^2$ (preferably, a range of 140 to 220 $mm^2$, and more preferably, a range of 146 to 210 $mm^2$). According to the third mode of the sixth aspect, the present invention has an arrangement in which the gas supply cylindrical portion of the first connector has a substantially circular cylindrical shape, an inner diameter of the gas supply cylindrical portion falls within a range of 10 to 20 mm (preferably, a range of 11.5 to 18.5 mm, and more preferably, a range of 12.5 to 17.5 mm), the gas passing opening has a substantially circular shape, and a diameter of the gas passing opening falls within a range of 8 to 12.5 mm (preferably, a range of 8.3 to 12 mm, and more preferably, a range of 8.6 to 11.6 mm). In the arrangement of at least one of the second and third modes of the sixth aspect, the first connector can be formed with a relatively small size and relatively low cost.

According to the seventh aspect, the present invention has an arrangement in which a pair of left and right ventilation holes are formed in positions of the mask main body, which correspond to left and right nostrils and their vicinities of the mask wearer, in a state in which the mask main body is put on the head of the mask wearer, and an opening area of each of the ventilation openings falls within a range of 630 to 1,260 mm$^2$ (preferably, a range of 760 to 1,180 mm$^2$, and more preferably, a range of 790 to 1,140 mm$^2$). In this arrangement, the pair of left and right relatively large ventilation holes are formed in the positions corresponding to the left and right nostrils and their vicinities of the mask wearer. Even when the mask wearer exhales a large amount of breath, therefore, the internal pressure of the mask main body does not rise, so the possibility that the mask wearer feels uncomfortable is relatively low. In addition, this arrangement decreases the possibility that a gas having risen in the mask main body flows out from the upper end and the vicinity of the mask main body, flows toward the eyes of the mask wearer, and dries the eyes of the mask wearer. This decreases the possibility that the mask wearer has discomfort on his or her eyes.

According to the eighth aspect, the present invention has an arrangement in which the above-mentioned gas supply mask apparatus is an oxygen mask apparatus. This arrangement can provide an oxygen mask apparatus capable of achieving the above-described effects achieved by each of the above-mentioned first to seventh aspects.

According to another exemplary embodiment, a gas mask supply connecting apparatus that connects a gas supply tube to a gas mask is disclosed, which comprises a first connector having a first gas opening through which a first gas exits the first connector and enters the gas mask in a first direction that corresponds to an axial direction of the first connector, and a second gas opening through which a second gas exits the first connector and enters the gas mask in a second direction that is substantially orthogonal to the axial direction of the first connector, such that the second gas surrounds an outer circumference of the first gas in a substantially ring-like shape inside the gas mask, and further comprises a second connector connected to the first connector; and a third connector connected to the second connector and the gas supply tube. The first, second, and third connectors may be integrally formed such that they are one piece.

The above, and other, objects, features and advantages of the present invention will become readily apparent from the following detailed description thereof which is to be read in connection with the accompanying drawings.

DETAILED DESCRIPTION OF THE INVENTION

Next, an oxygen mask apparatus according to an embodiment of the present invention will be explained with reference to FIGS. 1 to 9 by dividing the explanation into "1. Explanation of Oxygen Mask Main Body", "2. Explanation of First to Fourth Connectors and Gas Supply Tube", and "3. Explanation of State in Which Gas Is Blown to Mask Main Body".

1. Explanation of Oxygen Mask Main Body

Figure 2:
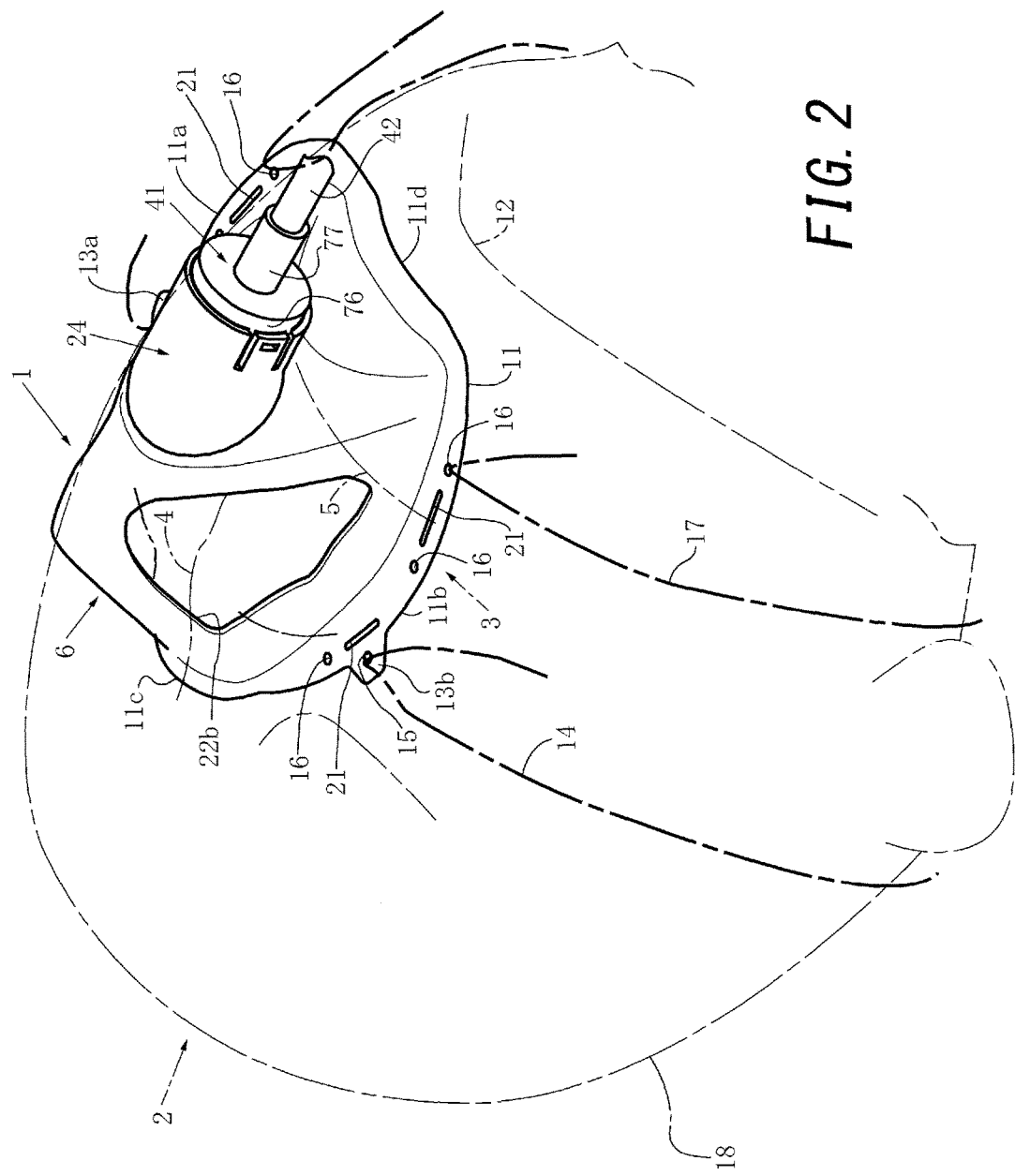
FIG. 2 is a perspective view showing a state in which the oxygen mask apparatus shown in FIG. 1 is in use.
Figure 5:
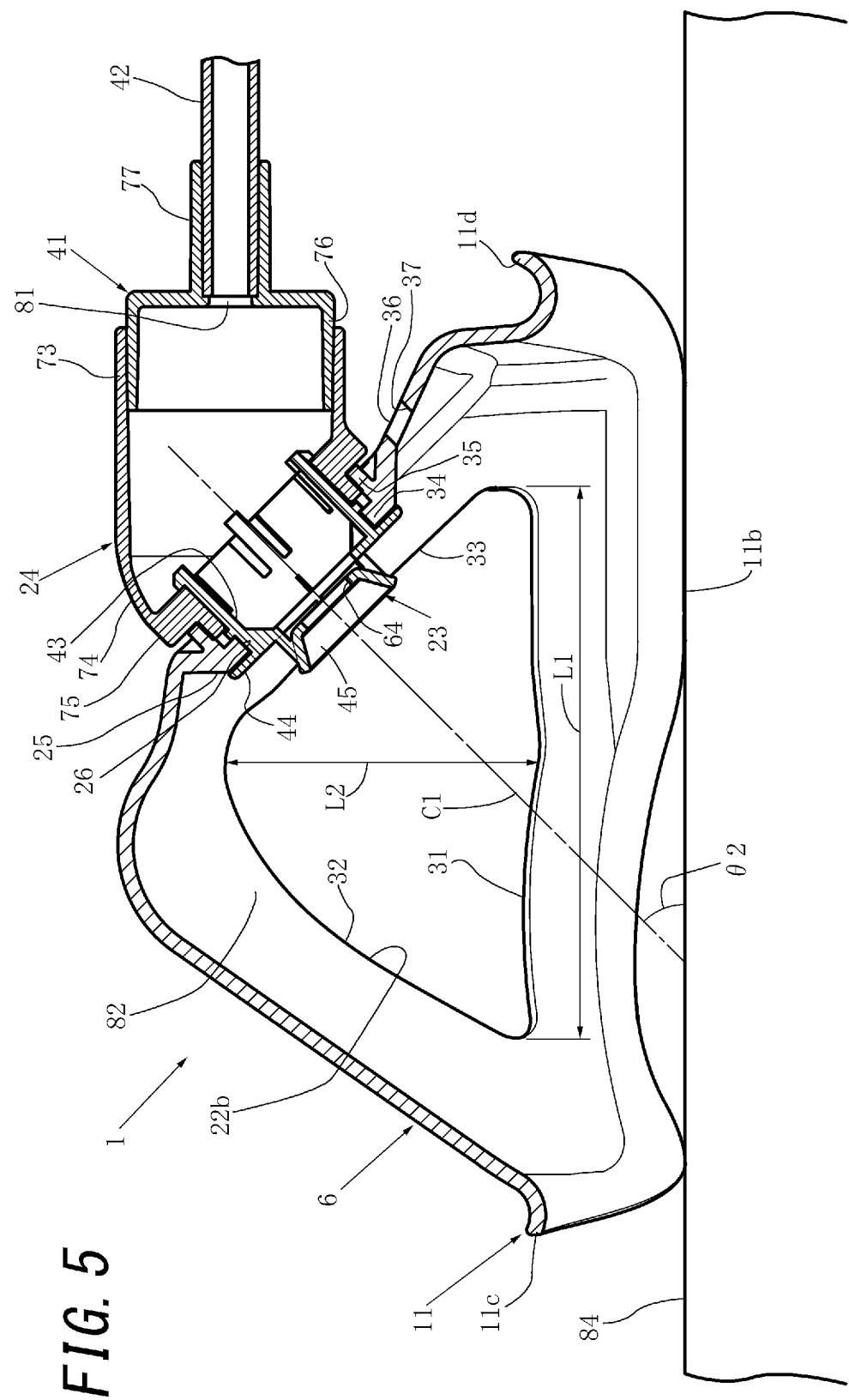
FIG. 5 is a longitudinal sectional view showing a state in which the oxygen mask apparatus shown in FIG. 1 is placed on a horizontal surface.

As shown in, e.g., FIGS. 2 and 5, an oxygen mask apparatus 1 as a gas supply mask apparatus includes a mask main body 6 capable of covering a substantially central portion (more specifically, a nose 4 and a mouth 5 and their peripheries) of a face 3 of a mask wearer 2 such as a patient. Note that the mask main body 6 can integrally be molded from a substantially transparent (in other words, light-transmitting) soft synthetic resin such as soft vinyl chloride so as to have a substantially bisymmetrical shape and substantially bisymmetrical pattern. At least left and right side portions 11a and 11b of an outer peripheral portion 11 of the mask main body 6 are so formed as to form a substantially flat surface over a substantially whole region (in other words, a substantially horizontal surface is formed when the mask main body 6 is placed upward on a horizontal surface 84 as shown in FIG. 5). Note that an upper side portion 11c of the outer peripheral portion 11 has a curved shape which slightly projects forward (in other words, outward), so as to substantially fit the shape of the nose 4 of the mask wearer 2. A lower side portion 11d of the outer peripheral portion 11 forms a substantially flat surface which substantially continues to the left and right side portions 11a and 11b, so as to substantially fit a portion (and the vicinity) above a chin 12 of the mask wearer 2. However, the lower side portion 11d may also have a curved shape which slightly projects forward, so as to substantially fit a portion (and the vicinity) below the chin 12 of the mask wearer 2.

Figure 3:
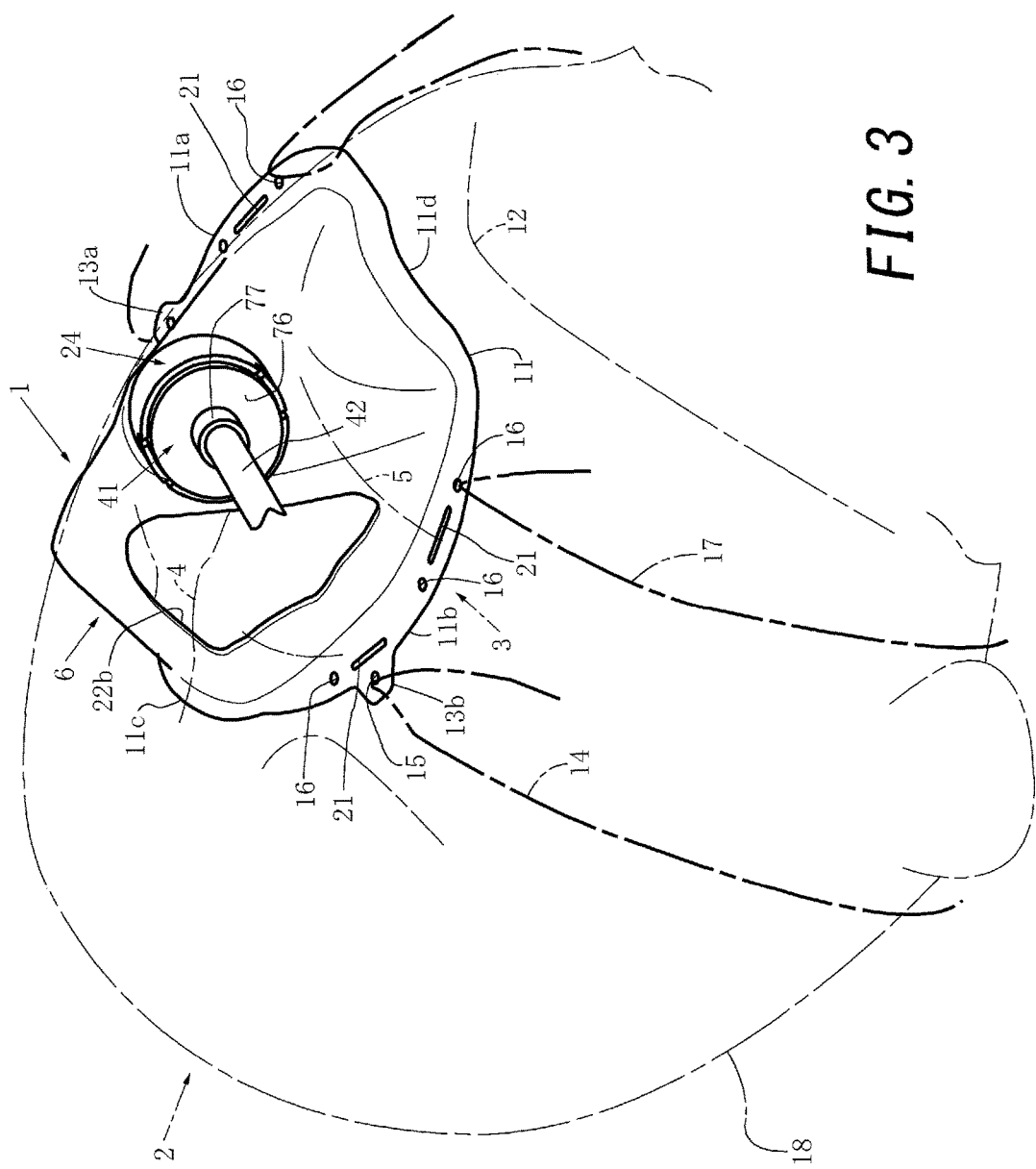
FIG. 3 is a perspective view of the oxygen mask apparatus similar to FIG. 2, in a state in which an oxygen supply tube is pivoted to the right.

As shown in, e.g., FIG. 3, in middle portions in a substantially vertical direction of the pair of left and right side portions 11a and 11b of the outer peripheral portion 11 of the mask main body 6, left and right projections 13a and 13b which project outward to the left and right into a substantially trapezoidal shape such as a substantially isosceles trapezoidal shape from the pair of left and right side portions 11a and 11b are formed. A pair of left and right insertion holes 15 is formed in the left and right projections 13a and 13b. The left and right end portions of a flat elastic string 14 as a flexible and elastic longitudinal attaching member are inserted into and attached to the insertion holes 15. Also, similar insertion holes 16 are arranged along a substantially longitudinal direction of each of the pair of left and right side portions 11a and 11b, and the number of insertion holes 16 is, e.g., three. Furthermore, each of the two ends of a second elastic string 17 which can be formed like the elastic string 14 may be inserted into and attached to one of the three insertion holes 16, in place of or in addition to the elastic string 14. A pair of upper and lower insertion slits 21 is formed in each of the pair of left and right side portions 11a and 11b. The upper one of the pair of upper and lower insertion slits 21 is adjacent to the insertion hole 15 (in other words, the projection 13a or 13b) in a substantially horizontal direction. Note that the two end portions of an elastic bandage as a flexible and elastic longitudinal attaching member can be inserted into and attached to a pair of left and right insertion slits of the insertion slits 21, instead of the flat elastic string 14. Note that each of the elastic strings 14 and 17 and elastic bandage is extended over a head (in other words, a head including the face of a person) 18 of the mask wearer 2, so as to pass over the left cheek, the back of the head, and the right cheek of the mask wearer 2.

As shown in, e.g., FIGS. 2 and 5, in slightly upper portions of the left and right sides of the mask main body 6, a pair of left and right ventilation holes 22a and 22b for communicating the inside and outside of the mask main body 6 are formed into flower patterns. Note that when the mask main body 6 is put on the mask wearer 2, the pair of left and right ventilation holes 22a and 22b are arranged in positions corresponding to the left and right nostrils of the mask wearer 2 and portions substantially around the left and right nostrils. The right ventilation hole 22b can have substantially the same bisymmetrical shape and bisymmetrical pattern as those of the left ventilation hole 22a. Also, a connector attaching portion 25 for attaching first and second connectors 23 and 24 is formed in a portion slightly below a substantially central portion of the mask main body 6. In addition, a hole 26 having a substantially pillar shape such as a circular pillar shape is formed in the connector attaching portion 25. The connector 25 is formed in the mask main body 6 so as to incline to the horizontal direction and vertical direction of the mask main body 6. The inclination direction of the connector attaching portion 25 can be a direction which projects outward from below to upward.

As shown in, e.g., FIGS. 2 and 5, each of the pair of left and right ventilation holes 22a and 22b having a substantially triangular shape has a substantially isosceles triangular shape whose three corners are rounded. When the mask main body 6 is put on the mask wearer 2, each of the pair of left and right ventilation holes 22a and 22b extends from the height of a substantially middle portion of the nose 4 in the vertical direction to a position slightly below a mouth 5 when viewed sideways. Note that as shown in FIG. 5, a base 31 of each of the pair of left and right ventilation holes 22a and 22b having a substantially triangular shape such as a substantially isosceles triangular shape is relatively adjacent to the left or right side portion 11a or 11b and extends substantially parallel to the left or right side portion 11a or 11b. Also, each of the pair of left and right ventilation holes 22a and 22b has upper and lower ridges 32 and 33 which extend from substantially two ends of the base 31 extending in a substantially vertical direction of the mask main body 6 toward the center in the horizontal direction of the mask main body 6 and connect to each other. Note that in this embodiment shown in the drawings, a linear length L1 approximated to the base 31 of each of the pair of left and right ventilation holes 22a and 22b is approximately 55 mm. Also, a height L2 of a substantially triangular shape, such as a substantially isosceles triangle, of the pair of left and right ventilation holes 22a and 22b is approximately 35 mm. The ratio of the height L2 to the length L1 is approximately 0.65. In addition, an opening area S1 of each of the pair of left and right ventilation holes 22a and 22b is approximately 950 mm$^2$ Furthermore, the numerical values of the length L1, height L2, and opening area S1 generally preferably fall within ranges described items (a) to (d) below from the viewpoint of practicality:

(a) the length L1: the range of 42 to 70 mm (more preferably, the range of 46 to 66 mm, and most preferably, the range of 48 to 64 mm), (b) the length L2: the range of 28 to 44 mm (more preferably, the range of 29 to 42 mm, and most preferably, the range of 30 to 40 mm), (c) the ratio L2/L2: the range of 0.52 to 0.82 (more preferably, the range of 0.54 to 0.78, and most preferably, the range of 0.56 to 0.76), and (d) the opening area S1: the range of 630 to 1,260 mm$^2$ (more preferably, the range of 760 to 1,180 mm$^2$, and most preferably, the range of 790 to 1,140 mm$^2$).

Figure 1:
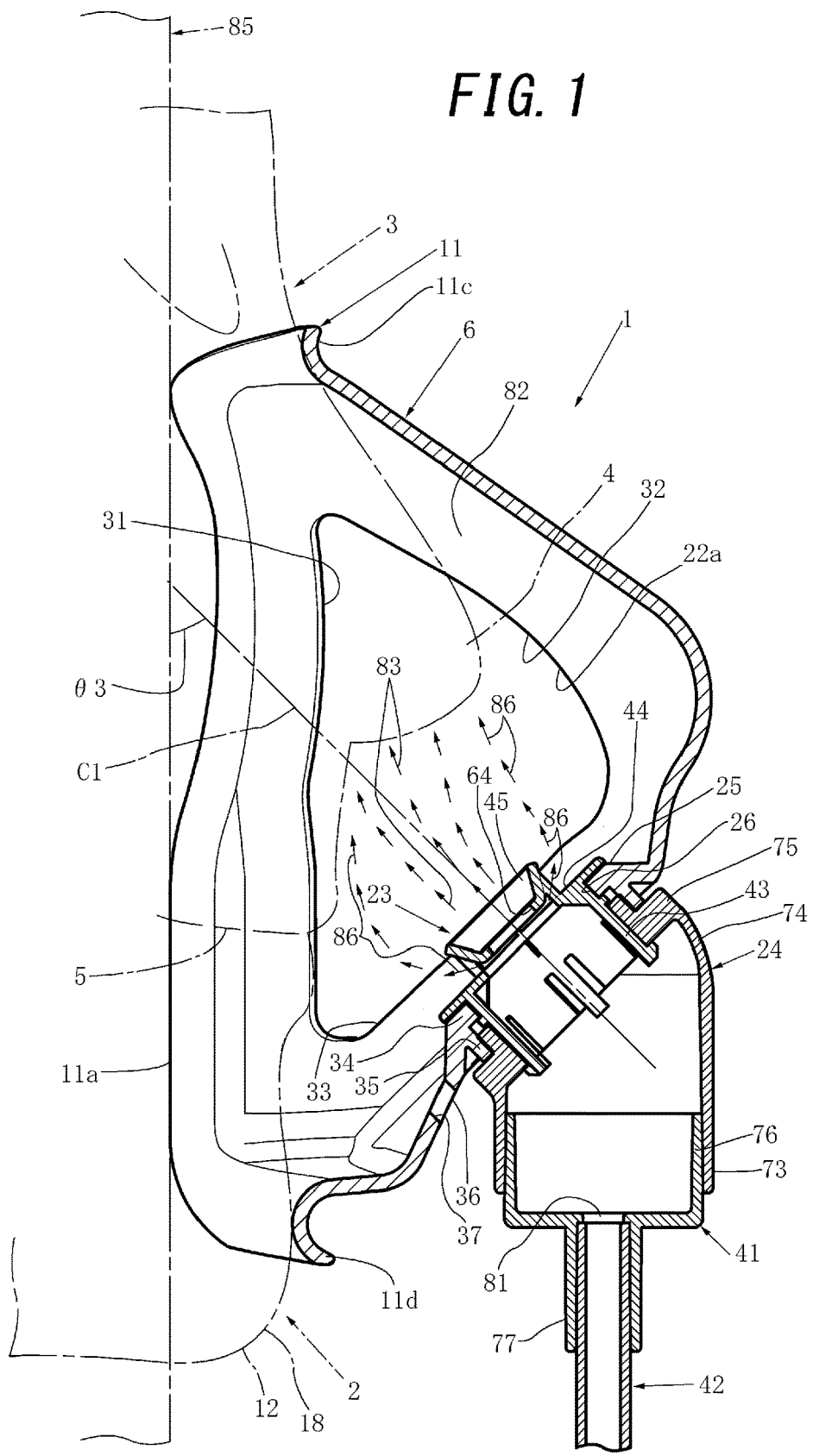
FIG. 1 is a longitudinal sectional view showing an embodiment in which the present invention is applied to an oxygen mask apparatus, in a state in which the oxygen mask apparatus is in use.

As shown in, e.g., FIGS. 1 and 5, the connector attaching portion 25 includes a substantially ring-like projecting wall 34 which projects toward the hole 26 so as to form the outer periphery of the hole 26, and a projecting wall 35 which projects outward from the outer periphery of the projecting wall 34 and its vicinity and has a substantially cylindrical shape such as a substantially circular cylindrical shape. Also, the connector attaching portion 25 (in other words, the ring-like projecting wall 34 and cylindrical projecting wall 35) is formed in the mask main body 6 so as to incline to the horizontal direction and vertical direction of the mask main body 6 in FIG. 5. This inclination direction of the connector attaching portion 25 in FIG. 5 can be a direction in which the connector attaching portion 25 projects outward from below. In addition, in a substantially lower portion of the connector attaching portion 25 in FIG. 5, a second connector attaching portion 36 capable of connecting a gas concentration measurement tube (not shown) is formed adjacent to the connector attaching portion 25. The second connector attaching portion 36 has a hole 37 such as a substantially circular hole. Furthermore, the second connector attaching portion 36 (in other words, the hole 37) is slightly inclined to the vertical direction in FIG. 5. This inclination direction of the second connector attaching portion 36 can be a direction in which the second connector attaching portion 36 slightly projects outward from below. Note that the above-mentioned gas concentration measurement tube can be used to measure the concentration of a gas such as carbon dioxide in the interior of the mask main body 6.

2. Explanation of First to Fourth Connectors and Gas Supply Tube

Figure 6:
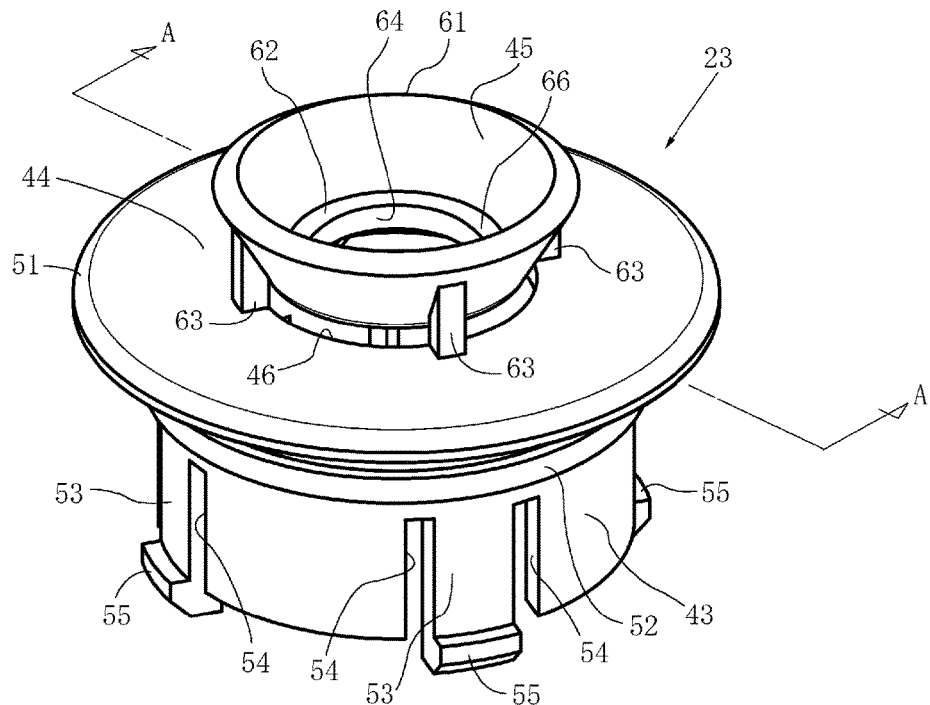
FIG. 6 is a perspective view of a first connector shown in FIG. 1.
Figure 7A:
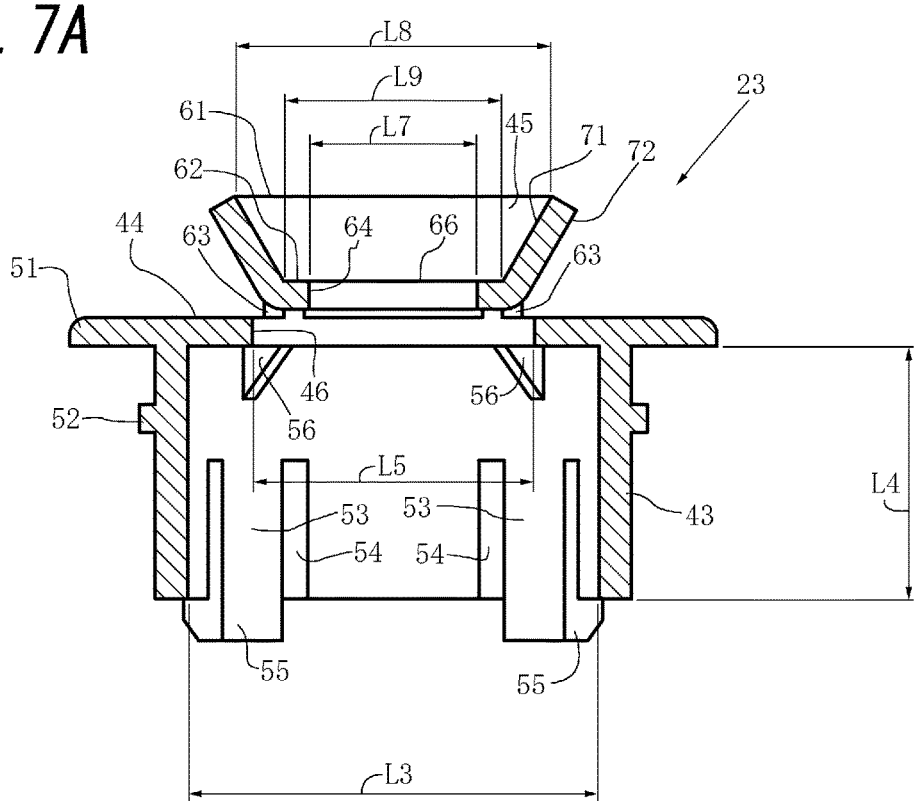
FIG. 7A is a sectional view taken along a line A-A in FIG. 6.

As shown in, e.g., FIGS. 1 and 5, the oxygen mask apparatus 1 includes the first connector 23, the second connector 24, a third connector 41, a gas supply tube 42, and a fourth connector (not shown). Note that each of the first to fourth connectors can be integrally molded from a substantially transparent (in other words, light-transmitting) hard synthetic resin such as hard vinyl chloride. Note also that the gas supply tube 42 can be integrally molded from a substantially transparent (in other words, light-transmitting) soft synthetic resin such as soft vinyl chloride. As shown in FIGS. 6 to 8, the first connector 23 includes a gas supply cylindrical portion 43 as a second cylindrical portion which extends along substantially an axial direction C1 of the first connector 23 and has a substantially cylindrical shape such as a substantially circular cylindrical shape, and an upper-end surface portion 44 which is integrated with the upper end of the cylindrical portion 43, and a gas straightening portion 45 which projects substantially upward along the axial direction C1 and substantially integrally from the upper-end surface portion 44 and the vicinity, and has a substantially inverted frustum shape (in other words, a substantially frustum shape in a substantially inverted state in the axial direction C1) such as a substantially inverted truncated conical shape (in other words, a substantially truncated conical shape in a substantially inverted state in the axial direction C1), and a substantially inverted truncated polygonal pyramidal shape (in other words, a substantially truncated polygonal pyramidal shape in a substantially inverted state in the axial direction C1). Also, a substantially circular or substantially polygonal gas passing opening 46 is formed in a substantially central portion of the upper-end surface portion 44. In addition, a substantially ring-like outward flange 51 projecting in a direction substantially perpendicular to the axial direction C1 is formed on the outer periphery of the upper-end surface portion 44. Furthermore, a second outer flange 52 having a substantially ring-like shape such as a substantially annular shape and projecting in a direction substantially perpendicular to the axial direction C1 is formed on the outer periphery of the cylindrical portion 43, which is close to the outside of the mask main body 6 in the axial direction C1 (in other words, close to the downside in FIG. 6) than the outward flange 51. Note that the second outward flange 52 can have substantially the same inner diameter as that of the outward flange 51, and an outer diameter much smaller than that of the outward flange 51.

As shown in FIGS. 6 to 8, the cylindrical portion 43 can have, e.g., four engaging arms 53 formed at preferably substantially equal angular intervals (for example, intervals of substantially 90°) along a substantially peripheral direction such as a substantially circumferential direction. Therefore, slits (or notches) 54 extending from the lower end to a middle portion in the axial direction are formed on the two sides of each of the four engaging arms 53 of the cylindrical portion 43. An engaging projection (or an engaging claw) 55 projects from the outer surface of the lower end portion of each engaging arm 53. Note that in each engaging arm 53, only the engaging projection 55 can project downward in the axial direction C1 (see FIG. 6) when compared to other portions of the cylindrical portion 43 except the engaging arm 53. When attaching the first connector 23 to the mask main body 6, the cylindrical portion 43 of the first connector 23 is inserted into the opening 26 from inside the mask main body 6. Note that by this insertion, the second outward flange 52 climbs over the ring-like projecting wall 34 of the mask main body 6 due to elastic deformation of the mask main body 6 and the like. Consequently, the ring-like projecting wall 34 of the mask main body 6 is clamped between the outward flange 51 of the first connector 23 and the second outward flange 52 of the first connector 23, so the first connector 23 is attached to the mask main body 6. Furthermore, reinforcing ribs 56 are formed in the first connector 23. The reinforcing ribs 56 are integrally molded so as to extend over the inner circumferential surface of the cylindrical portion 43 and the outer surface (in other words, the lower side) in the axial direction C1 of the upper-end surface portion 44. Note that in the embodiment shown in the drawings, four reinforcing ribs 56 are formed at substantially equal intervals.

As shown in, e.g., FIGS. 6 to 8, the gas straightening portion 45 having an inverted frustum shape or the like is formed to have a substantially hollow portion in which an upper surface 61 in the axial direction C1 of the gas straightening portion 45 is substantially entirely open. On the lower-end side in the axial direction C1 of the gas straightening portion 45, an inward flange 62 having a substantially ring-like shape such as a substantially circular ring-like shape or substantially polygonal ring-like shape is formed integrally with the gas straightening portion 45. In the lower-end portion of the gas straightening portion 45, therefore, a lower-end opening 64 having, e.g., a substantially circular shape or substantially polygonal shape is formed as a first gas introduction opening. Also, the gas straightening portion 45 is formed on the upper surface of the upper-end surface portion 44 by a plurality of (e.g., four) posts 63 which are formed integrally with the outer surface of the gas straightening portion 45 and the upper surface of the upper-end surface portion 44. Note that the posts 63 can be arranged at substantially equal intervals (in other words, at intervals of substantially 90°).

In the embodiment shown in the drawings, the cylindrical portion 43, having a substantially circular cylindrical shape, of the first connector 23 shown in, e.g., FIGS. 6 to 8 has an inner diameter L3 of approximately 15 mm, a length L4 of approximately 9 mm in the axial direction C1, and an inside area of approximately 176 mm$^2$ in a direction substantially perpendicular to the axial direction C1. Also, in the embodiment shown in the drawings, the gas passing opening 46 of the first connector 23 has a diameter L5 of approximately 10 mm, and an opening area of approximately 78 mm$^2$, which indicates the size of the opening 46. In addition, in the embodiment shown in the drawings, a spacing (or an opening width) L6 of a substantially ring-like gas outlet 65 formed between the upper-end surface portion 44 and gas straightening portion 45 (in other words, the narrowest space between the upper-end surface portion 44 and gas straightening portion 45) is approximately 0.7 mm. Furthermore, an angle θ1 which a direction C2 perpendicular to the gas outlet 65 as a second gas introduction opening makes with the axial direction C1 of the gas straightening portion 45 is approximately 50°. Also, in the embodiment shown in the drawings, a diameter L7 of the opening 64 is approximately 6 mm. In the embodiment shown in the drawings, an inner-circumferential diameter L8 of the upper surface 61 of the gas straightening portion 45 is approximately 12 mm. A diameter L9 of the lower surface 66 of the gas straightening portion 45 is approximately 7.8 mm. The inclination angle of each of an inner circumferential surface 71 and outer circumferential surface 72 of the gas straightening portion 45 with respect to the axial direction C1 is approximately 30°.

The numerical values of these portions such as the inner diameter L3 of the first connector 23 generally preferably fall within ranges described in items (a) to (k) below from the viewpoint of practicality:

(a) the inner diameter (in other words, a maximum length of the inner circumferential surface in a planar view) L3 of the cylindrical portion 43 having a substantially circular cylindrical shape or the like: the range of 10 to 20 mm (more preferably, the range of 11.5 to 18.5 mm, and most preferably, the range of 12.5 to 17.5 mm), (b) the length L4 of the cylindrical portion 43 having a substantially cylindrical shape such as a substantially circular cylindrical shape in the axial direction C1: the range of 6 to 12 mm (more preferably, the range of 6.5 to 11.5 mm, and most preferably, the range of 7.2 to 10.8 mm), (c) the inside area of the cylindrical portion 43 having a substantially cylindrical shape such as a substantially circular cylindrical shape in the direction substantially perpendicular to the axial direction C1: the range of 118 to 236 mm$^2$ (more preferably, the range of 140 to 220 mm$^2$, and most preferably, the range of 146 to 210 mm$^2$), (d) the diameter (in other words, a maximum length of the inner circumferential surface in a planar view) L5 of the gas passing opening 46: the range of 8 to 12.5 mm (more preferably, the range of 8.3 to 12 mm, and most preferably, the range of 8.6 to 11.6 mm), (e) the opening area of the gas introduction opening 46: the range of 52 to 104 mm$^2$ (more preferably, the range of 62.4 to 97.5 mm$^2$, and most preferably, the range of 65 to 93.6 mm$^2$), (f) the spacing L6 of the substantially ring-like gas outlet 65: the range of 0.56 to 0.88 mm (more preferably, the range of 0.58 to 0.84 mm, and most preferably, the range of 0.6 to 0.82 mm), (g) the angle 81 which the gas outlet 65 makes with the axial direction C1: the range of 40° to 62° (more preferably, the range of 42° to 60°, and most preferably, 44° to 58°), (h) the diameter (in other words, a maximum length of the inner circumferential surface in a planar view) L7 of the lower-end opening 64 of the gas straightening portion 45: the range of 4.8 to 7.6 mm (more preferably, the range of 5 to 7.2 mm, and most preferably, the range of 5.2 to 7 mm), (i) the inner circumferential diameter (in other words, a maximum length of the inner circumference of the upper surface 61 in a planar view) L8 of the upper surface 61 of the gas straightening portion 45: the range of 9.6 to 15 mm (more preferably, the range of 10 to 14.4 mm, and most preferably, the range of 10.4 to 14 mm), (j) the inner circumferential diameter (in other words, a maximum length of the inner circumference of the lower surface 66) L9 of the lower surface 66 of the gas straightening portion 45: the range of 6.2 to 9.8 mm (more preferably, the range of 6.5 to 9.4 mm, and most preferably, the range of 6.7 to 9.1 mm), and (k) the inclination angle of each of the inner circumferential surface 71 and outer circumferential surface 72 of the gas straightening portion 45 with respect to the axial direction C1: the range of 24° to 37.5° (more preferably, the range of 25° to 36°, and most preferably, the range of 26° to 35°).

As shown in, e.g., FIGS. 1 and 5, a portion on the lower-end side of the second connector 24 forms, as a first cylindrical portion, a lower cylindrical portion 73 having a substantially cylindrical shape such as a substantially circular cylindrical shape to which the third connector 41 is attached. Note that in the state shown in FIG. 1, the lower cylindrical portion 73 extends in a substantially vertical direction. A portion on the upper-end side of the second connector 24 is obliquely bent upward from the portion on the lower-end side of the second connector 24, so as to extend along substantially the axial direction C1. An upper cylindrical portion 74 having a substantially cylindrical shape such as a substantially circular cylindrical shape as a second cylindrical portion near the upper end and its vicinity of the second connector 24 is inserted between the gas supply cylindrical portion 43 of the first connector 23 and the cylindrical projecting wall 35 of the mask main body 6. By this insertion, a ring-like upper wall 75 of the second connector 24 abuts against the lower end of the cylindrical projecting wall 35 of the mask main body 6. Also, the engaging projections 55 of the engaging arms 53 of the first connector 23 engage with the lower surface of the ring-like upper wall 75 in order to prevent removal. As a consequence, the second connector 24 can be attached to the first connector 23 in a state in which the second connector 24 relatively easily pivots with respect to the first connector 23. In addition, as shown in, e.g., FIGS. 1 and 2, the third connector 41 includes a large-diameter, closed-end cylindrical portion 76 having a circular cylindrical shape or the like, and a small-diameter cylindrical portion 77 having a circular cylindrical shape or the like and connected to the lower end portion of the cylindrical portion 76 by integral molding or the like. Note that a through hole 81 for communicating with the cylindrical portion 77 is formed in a substantially central position of the bottom of the cylindrical portion 76. One end portion of the gas supply tube 42 is inserted into and connected to the small-diameter cylindrical portion 77. Also, the upper-end opening of the gas supply tube 42 communicates with the large-diameter cylindrical portion 76 as a third cylindrical portion through the through hole 81. Furthermore, the above-mentioned fourth connector (not shown) is connected to the other end portion of the gas supply tube 42. The fourth connector can be connected to a gas cylinder (not shown) such as an oxygen cylinder or to a gas supply nozzle (not shown) installed in a hospital room as needed.

3. Explanation of State in which Gas is Blown to Mask Main Body

When the oxygen mask apparatus 1 is put on the face 3 of the mask wearer 2 as shown in, e.g., FIG. 1, the direction of a gas flow 83 (in other words, the direction in which the upper surface 61 of the gas straightening portion 45 points) supplied from the gas straightening portion 45 of the first connector 23 to a space 82 in the mask main body 6 (in other words, a gas introduction space existing between the face 3 and mask main body 6) substantially matches the axial direction C1 in at least the initial stage of supply. When the oxygen mask apparatus 1 (in other words, the mask main body 6) is placed upward on a horizontal surface 84 as shown in FIG. 5 (this state will be referred to as "the mask placement state shown in FIG. 5" hereinafter), the axial direction C1 extends in a substantially vertical direction of the mask main body 6 (in other words, the oxygen mask apparatus 1) in a planar view. In a planar view, therefore, the axial direction C1 substantially matches a virtual bisecting central line (in other words, a central line extending in the vertical direction of the mask main body 6) which bisects the mask main body 6 (in other words, the oxygen mask apparatus 1) shown in FIG. 5 into left and right halves when viewed from above, so the angle formed between them is substantially 0° in a planar view. Also, in the mask placement state shown in FIG. 5, the axial direction C1 linearly extends in an oblique direction from a portion close to the upper portion 11c of the mask main body 6 (in other words, the oxygen mask apparatus 1) to a portion close to the lower portion 11d of the mask main body 6, and slightly upward. An angle 82 formed between the axial direction C1 and horizontal surface 84 is substantially 45° when the mask main body 6 is viewed from the side (in other words, in the mask placement state shown in FIG. 5). Furthermore, FIG. 1 shows a mask wearing state (to be referred to as "the correct mask wearing state shown in FIG. 1" hereinafter) in which a person (in other words, the mask wearer 2) having an average body shape and average head shape is correctly wearing the oxygen mask apparatus 1 (in other words, the mask main body 6) and facing forward. Note that when compared to the state in which the oxygen mask apparatus 1 is placed upward on the horizontal surface 84 as shown in FIG. 5, a substantially only difference of this correct mask wearing state shown in FIG. 1 is that the oxygen mask apparatus 1 is raised approximately 90°. Accordingly, the horizontal surface 84 in FIG. 5 is replaced with a virtual perpendicular plane (in other words, a virtual vertical plane) 85 in FIG. 1. Also, the angle 82 in FIG. 5 is replaced with an angle 83 in FIG. 1. Note that in order to achieve the object of the present invention, each of the angles 82 and 83 generally preferably falls within the range of 30° to 60°, more preferably, the range of 35° to 55°, and most preferably, the range of 40° to 50°, from the viewpoint of practicality. In addition, in order to achieve the object of the present invention, an angle 84 (not shown) which the axial direction C1 makes with a virtual bisecting central line (in other words, a bisecting central line extending from the upper portion 11c to the lower portion 11d of the mask main body 6) which bisects the mask main body 6 (in other words, the oxygen mask apparatus 1) into left and right halves when the mask main body 6 is viewed frontways generally preferably falls within the range of 0° to 15°, more preferably, the range of 0° to 10°, and most preferably, the range of 0° to 5°, from the viewpoint of practicality.

When a gas such as oxygen gas is supplied to the above-mentioned fourth connector in the mask wearing state in which the mask wearer 2 is wearing the oxygen mask apparatus 1 as shown in, e.g., FIGS. 1 and 6, this gas is supplied from the fourth connector to the second connector 24 through the gas supply tube 42 and third connector 41. The gas supplied to the second connector 24 is supplied from the second connector 24 to the gas supply cylindrical portion 43 of the first connector 23. In addition, one half (to be referred to as "the above-mentioned first gas or the like" hereinafter) of the gas supplied to the gas supply cylindrical portion 43 of the first connector 23 is supplied into the gas straightening portion 45 through the gas passing opening 46 and lower-end opening 64, and then supplied inside the mask main body 6 from the upper surface 61 via the gas straightening portion 45. The other half (to be referred to as "the above-mentioned second gas or the like" hereinafter) of the above-mentioned gas is supplied inside the mask main body 6 through the gas passing opening 46 and gas outlet 65.

Figure 7B:
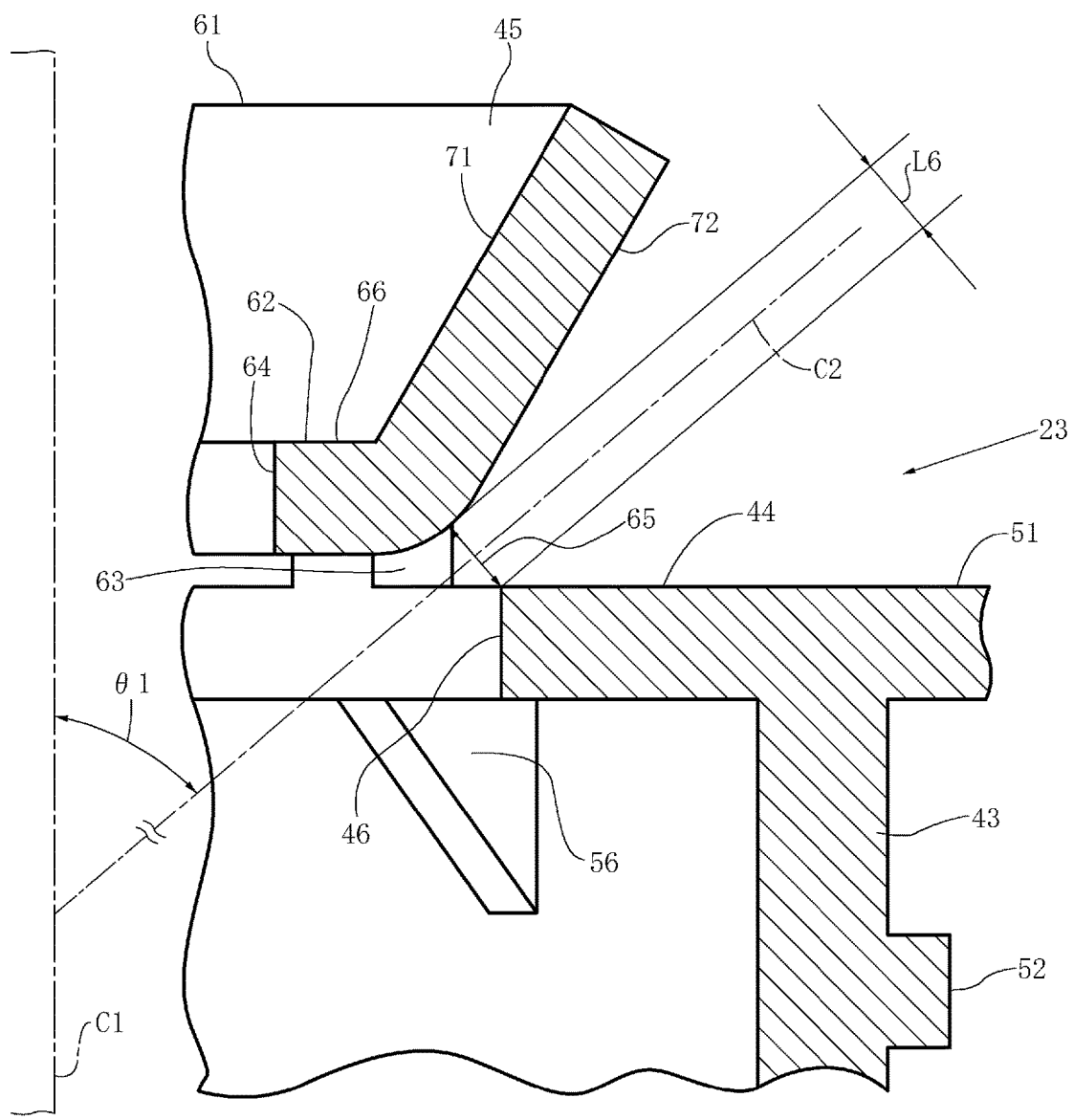
FIG. 7B is a partially enlarged view of FIG. 7A.
Figure 8:
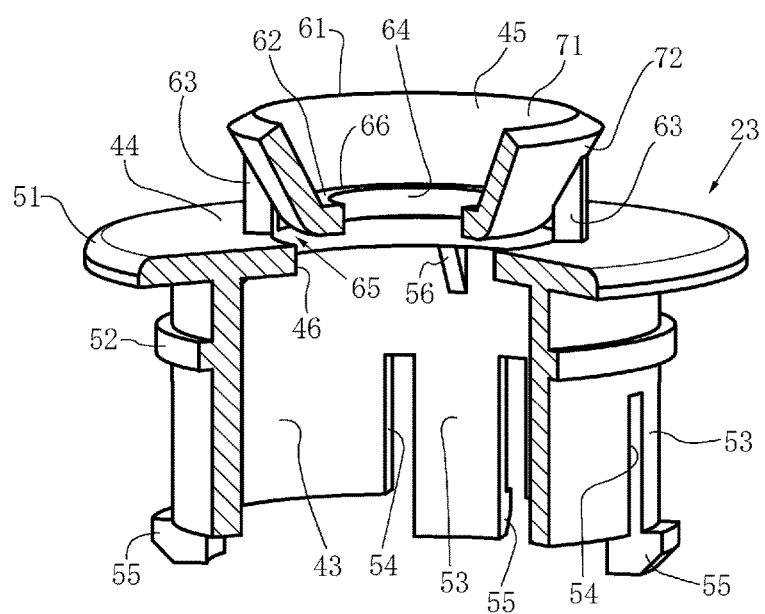
FIG. 8 is a partially cutaway perspective view of a portion of the first connector shown in FIG. 6.

As shown in, e.g., FIGS. 1 and 7B, the gas flow 83 of the above-mentioned first gas supplied inside the mask main body 6 as described above is supplied inside the mask main body 6 from the gas straightening portion 45 in a direction substantially along the axial direction C1. Also, a gas flow 86 of the above-mentioned second gas is supplied inside the mask main body 6 from the gas passing opening 46 in a direction substantially along the perpendicular direction C2. When the mask wearer 2 breathes in, as shown in FIG. 1, the gas flow 83 of the above-mentioned first gas deflects toward a substantially lower end of the nostril of the mask wearer 2. Accordingly, the mask wearer 2 can effectively inhale the gas flow 83 of the above-mentioned first gas from the nose 4. By contrast, the gas flow 86 of the above-mentioned second gas is influenced by the existence of the outer circumferential surface 72 of the gas straightening portion 45, and the blowing direction of the gas outlet 65 (in other words, the perpendicular direction C2). Therefore, when the mask wearer 2 breathes in, for example, an extremely large amount of the gas flow 86 of the above-mentioned second gas does not join the gas flow 83 of the above-mentioned first gas or the like. Then, the gas flow 86 of the above-mentioned second gas starts flowing apart from the first connector 23 so as to surround, in a substantially ring-like shape, the outer circumference of the gas flow 83 of the above-mentioned first gas at a slight distance between them.

Also, when the gas flow 83 of the above-mentioned first gas and the gas flow 86 of the above-mentioned second gas flow as described above, the mask wearer 2 can effectively inhale both the above-mentioned first gas and above-mentioned second gas from the nostrils when, for example, he or she breathes in. In addition, when the mask wearer 2 does not breath in, for example, the gas flow 86 of the above-mentioned second gas surrounds the outer circumference of the gas flow 83 of the above-mentioned first gas in a substantially ring-like shape. This makes it possible to effectively prevent the above-mentioned first gas from leaking outside the mask main body 6 from, e.g., the pair of left and right ventilation holes 22a and 22b.

Figure 9:
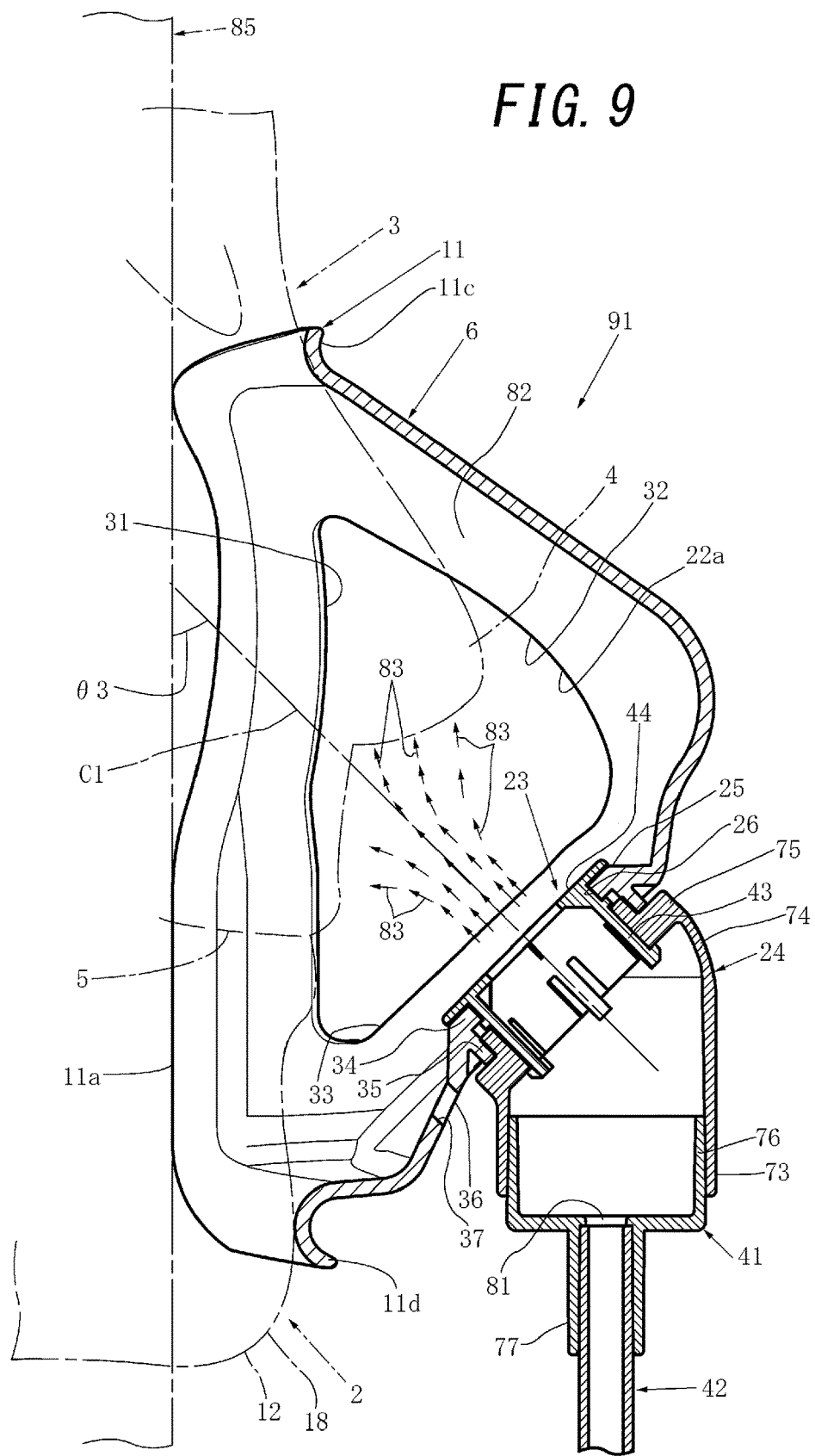
FIG. 9 is a longitudinal sectional view showing a state in which an oxygen mask apparatus according to a reference example of the present invention is in use.
Figure 10:
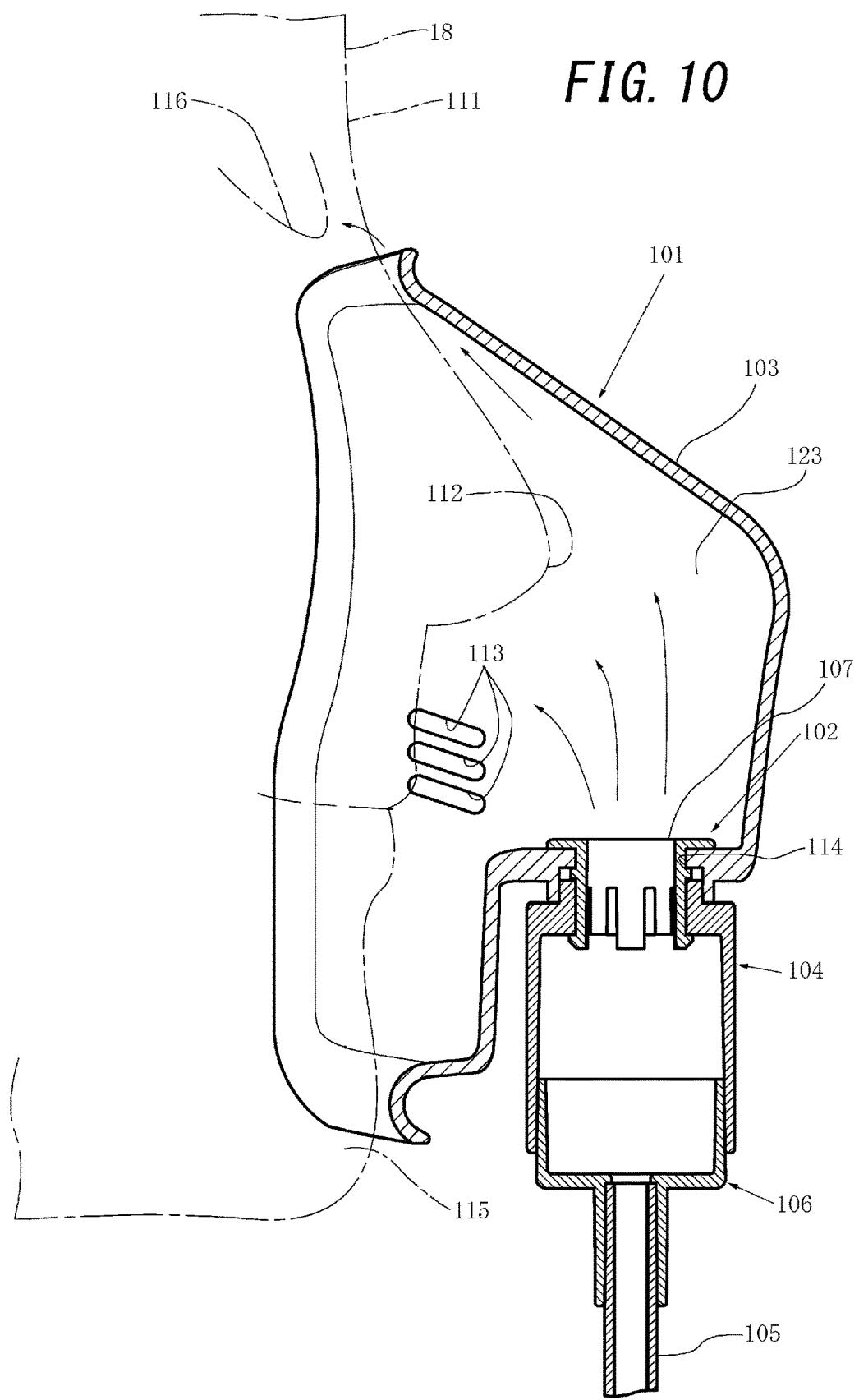
FIG. 10 is a longitudinal sectional view showing a state in which a conventional oxygen mask apparatus is in use.
Figure 11:
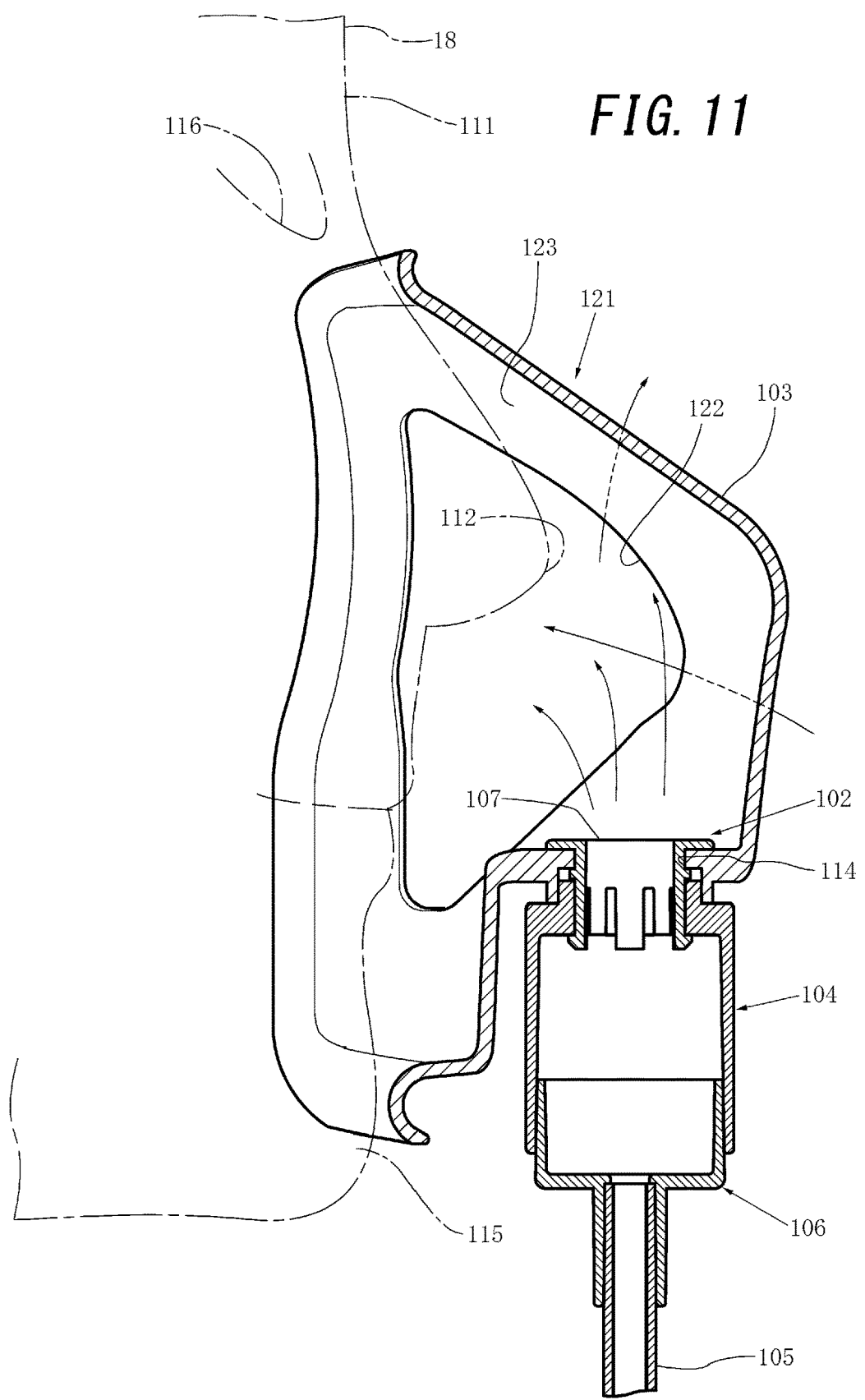
FIG. 11 is a longitudinal sectional view showing a state in which an oxygen mask apparatus as a modification of the conventional oxygen mask apparatus shown in FIG. 10 is in use.

FIG. 9 shows an oxygen mask apparatus (to be referred to as "the mask apparatus of the above-mentioned reference example" hereinafter) 91 according to a reference example of the present invention. When compared to the arrangement of the oxygen mask apparatus (to be referred to as "the mask apparatus of the above-mentioned embodiment" hereinafter) 1 according to the embodiment of the present invention shown in FIG. 1 and the like, the only difference of the mask apparatus 91 of the above-mentioned reference example is the arrangement of only the first connector 23. More specifically, in the mask apparatus 91 of the above-mentioned reference example, the gas straightening portion 45 of the first connector 23 of the mask apparatus 1 of the above-mentioned embodiment and the four posts 63 connecting the gas straightening portion 45 to the upper-end surface portion 44 are omitted. In the mask apparatus 91 of the above-mentioned reference example, a substantially whole of a gas supplied from the second connector 24 to the gas supply cylindrical portion 43 of the first connector 23 is supplied inside the mask main body 6 through the gas passing opening 46. As shown in FIG. 9, therefore, the gas flow 83 of the gas supplied inside the mask main body 6 as described above is supplied inside the mask main body 6 from the gas passing opening 46 in the direction substantially along the axial direction C1. When the mask wearer 2 breathes in, as shown in FIG. 9, the gas flow 83 of the gas slightly deflects toward a substantially lower end of the nostril of the mask wearer 2. Accordingly, the mask wearer 2 can inhale the gas flow 83 of the gas from the nose 4. In the above-mentioned reference example shown in FIG. 9, however, the gas flow 86 of the above-mentioned second gas surrounding the gas flow 83 of the gas in a substantially ring-like shape as in the case of the embodiment shown in FIG. 1 does not exist. Therefore, the gas leaks outside the oxygen mask apparatus 1 through, e.g., the pair of left and right relatively large ventilation holes 22a and 22b. Consequently, a large amount of air or the like mixes in the gas supplied to the nostrils and their vicinities of the mask wearer 2, so the mask wearer 2 inhales, from the nostrils, the gas in which the large amount of air and the like has mixed and the oxygen concentration has decreased. This decreases the effect of inhaling the gas by the mask wearer 2, and the gas uselessly vanishes outside the oxygen mask apparatus 1.

Figure 4:
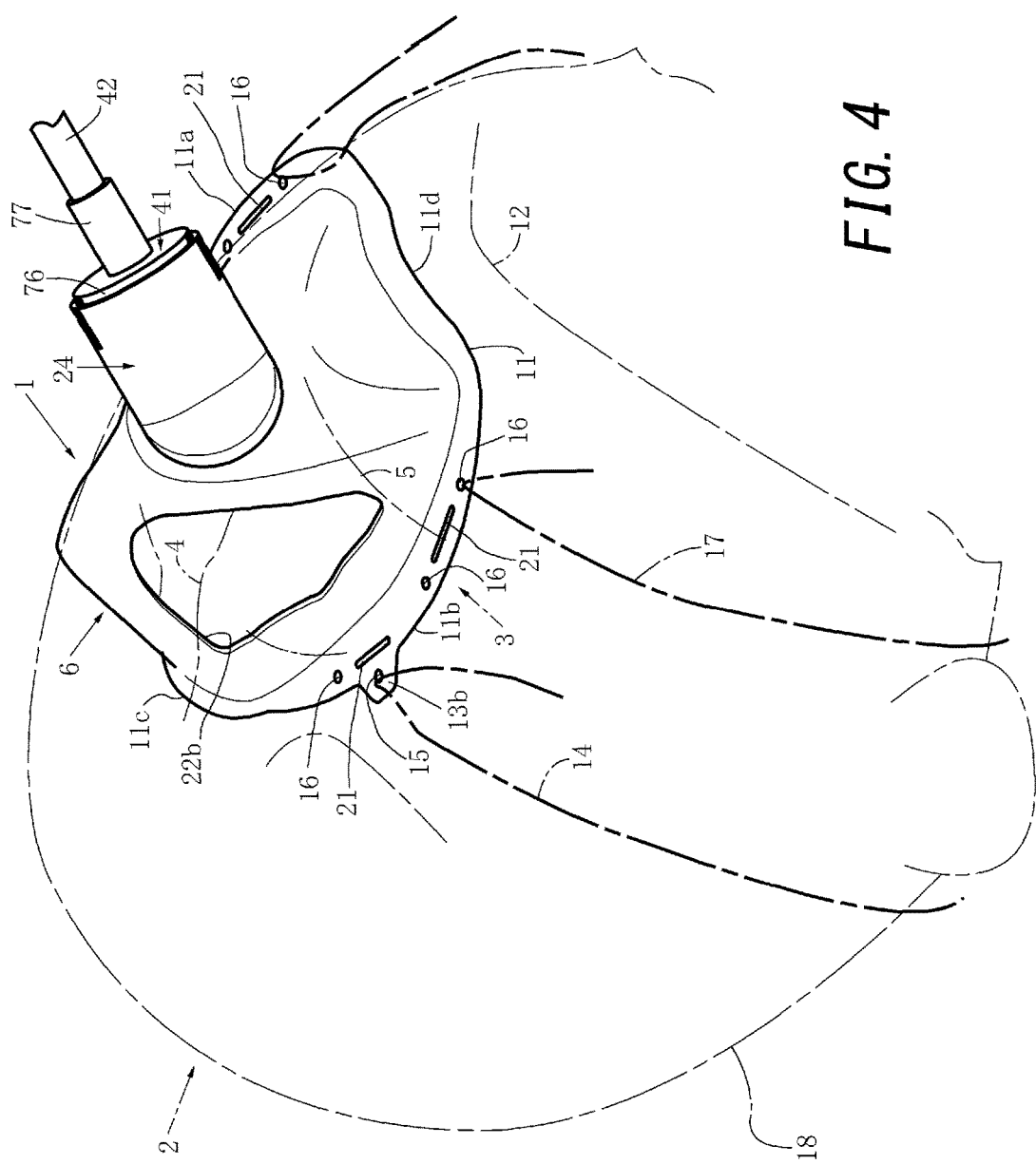
FIG. 4 is a perspective view of the oxygen mask apparatus similar to FIG. 2, in a state in which the oxygen supply tube is pivoted to the left.

When the gas supply tube 42 is not shifted to the left or right as shown in FIG. 2 when viewed frontways, the second connector 24 is positioned substantially just below the lower end in the axial direction C1 of the first connector 23 as shown in, e.g., FIGS. 1 and 2. However, when the gas supply tube 42 moves forward to the right side of the mask main body 6 as shown in FIG. 3 from the state shown in FIG. 2 for some reason, the second connector 24 pivots forward clockwise in FIG. 2 with respect to the first connector 23 (in other words, the mask main body 6). Even in a case like this, therefore, the gas supply tube 42 is not particularly twisted or bent, and holds a substantially normal gas supply state. When the gas supply tube 42 moves backward from the state shown in FIG. 3 to the state shown in FIG. 2, the second connector 24 pivots backward counterclockwise in FIG. 3 with respect to the first connector 23 (in other words, the mask main body 6). Even in a case like this, therefore, the gas supply tube 42 is not particularly twisted or bent, and holds a substantially normal gas supply state. Furthermore, when the gas supply tube 42 moves forward to the left side of the mask main body 6 as shown in FIG. 4 from the state shown in FIG. 2 for some reason, the second connector 24 pivots forward counterclockwise in FIG. 2 with respect to the first connector 23 (in other words, the mask main body 6). Even in a case like this, therefore, the gas supply tube 42 is not particularly twisted or bent, and holds a substantially normal gas supply state. When the gas supply tube 42 moves backward from the state shown in FIG. 4 to the state shown in FIG. 2, the second connector 24 pivots backward clockwise in FIG. 3 with respect to the first connector 23 (in other words, the mask main body 6). Even in a case like this, therefore, the gas supply tube 42 is not particularly unnecessarily twisted or bent, and holds a substantially normal gas supply state.

Having described a specific preferred embodiment of the present invention with reference to the accompanying drawings, it is to be understood that the invention is not limited to this precise embodiment, and that various changes and modifications may be effected therein by one skilled in the art without departing from the scope or spirit of the invention as defined in the appended claims.

For example, the first connector 23 and second connector 24 are separate in the above-described embodiment. However, the first connector 23 and second connector 24 can also be integrated.

In addition, the second connector 24 and third connector 41 are separate in the above-described embodiment. However, the second connector 24 and third connector 41 can also be integrated.

Also, in the above-described embodiment, each of the pair of left and right ventilation holes 22a and 22b is formed into a substantially triangular shape having a substantially bisymmetrical shape. However, each of the pair of left and right ventilation holes 22a and 22b need not have a substantially triangular shape, and may also have another shape such as a substantially semi-circular shape, an oval shape, a substantially elliptical shape, or a substantially polygonal shape (except a substantially triangular shape).

Furthermore, the lower-end opening 64 of the gas straightening portion 45 is formed into a substantially circular shape in the above-described embodiment. However, the lower end-opening 64 need not be formed into a substantially circular shape, and may also have a polygonal shape such as a substantially hexagonal shape or substantially octagonal shape, an elliptical shape, a substantially oval shape, or a substantially ring-like shape.

The invention claimed is:

1. A gas supply mask apparatus comprising:
   a mask main body configured to be worn on the head of a mask wearer;
   a first gas introduction opening configured to introduce a first gas to a gas introduction space existing between the face of the mask wearer and the mask main body; and
   a second gas introduction opening configured to introduce a second gas in a substantially ring-like state to the gas introduction space, such that the second gas substantially surrounds the first gas.

2. The apparatus of claim 1, wherein the first gas introduction opening is configured to introduce the first gas in a substantially bundle-like state to the gas introduction space.

3. The apparatus of claim 1, wherein the first gas introduction opening introduces the first gas to the gas introduction space in a first introduction direction, the second gas introduction opening introduces the second gas to the gas introduction space in a second introduction direction, and an angle which the second introduction direction makes with the first introduction direction falls within a range of 40° to 62°.

4. The apparatus of claim 3, wherein the angle which the second introduction direction makes with the first introduction direction falls within a range of 42° to 60°.

5. The apparatus of claim 3, wherein the angle which the second introduction direction makes with the first introduction direction falls within a range of 44° to 58°.

6. The apparatus of claim 1, wherein, when the mask main body is placed upward on a horizontal surface, a first angle falling within a range of 30° to 60° is formed between the horizontal surface and a direction in which the first gas introduction opening faces when the mask main body is viewed from the side, and a second angle falling within a range of 0° to 15° is formed between the direction in which the first gas introduction opening faces and a central line which bisects the mask main body into left and right halves when the mask main body is viewed from above.

7. The apparatus of claim 6, wherein the first angle falls within a range of 35° to 55° and the second angle falls within a range of 0° to 10°.

8. The apparatus of claim 6, wherein the first angle falls within a range of 40° to 50° and the second angle falls within a range of 0° to 5°.

9. The apparatus of claim 1, wherein, when a mask wearer is correctly wearing the mask main body and facing forward, a third angle between 30° and 60° is formed between the direction the first gas introduction opening faces and a virtual vertical plane facing forward when the mask main body is viewed from the side, and a fourth angle between 0° and 15° is formed between the direction in which the first gas introduction opening faces and a central line which bisects the mask main body into left and right halves when the mask main body is viewed frontways.

10. The apparatus of claim 9, wherein the third angle falls within a range of 35° to 55° and the fourth angle falls within a range of 0° to 10°.

11. The apparatus of claim 9, wherein the third angle falls within a range of 40° to 50° and the fourth angle falls within a range of 0° to 5°.

12. The apparatus of claim 1, further comprising:
    a gas supply cylindrical portion extending substantially along the direction in which the first gas introduction opening faces;
    a gas straightening portion having a substantially inverted frustum shape and formed on an upper-end side of the gas supply cylindrical portion so as to project from the upper-end side; and
    a gas outlet formed into a substantially ring-like shape between the gas straightening portion and the gas supply cylindrical portion.

13. The apparatus of claim 1, further comprising a gas supply cylindrical portion configured to supply a gas into the mask main body from outside the mask main body through a gas passing opening, the first gas introduction opening and the second gas introduction opening,
    wherein the gas supply cylindrical portion comprises a first cylindrical portion configured to transfer the gas substantially upward, and a second cylindrical portion connected to an upper portion of said first cylindrical portion, and the second cylindrical portion is configured to supply the gas to the first gas instruction opening and the second gas introduction opening after deflecting a direction of a flow of the gas supplied from the first cylindrical portion to a direction in which the first gas introduction opening faces.

14. The apparatus of claim 1, further comprising:
a first connector comprising the first gas introduction opening and the second gas instruction opening, and
a second connector connected to the first connector to extend outside said the mask main body,
wherein the second connector comprises a lower cylindrical portion extending substantially downward, and an upper cylindrical portion integrated with the lower cylindrical portion to extend obliquely upward in a bent state from the lower cylindrical portion, and
the upper cylindrical portion is configured to be pivotal with respect to the first connector.

15. The apparatus of claim 14, wherein the first connector comprises a gas supply cylindrical portion extending substantially along a direction in which the first gas introduction opening faces, a gas straightening portion having a substantially inverted frustum shape and formed on an upper-end side of the gas supply cylindrical portion to project from the upper-end side, and a gas outlet formed into a substantially ring-like shape between the gas straightening portion and the gas supply cylindrical portion.

16. The apparatus of claim 15, wherein the length of the gas supply cylindrical portion in a first direction in which the first gas introduction opening of the first connector faces falls within a range of 6 to 12 mm, and an inside area of the first connector in a direction substantially perpendicular to the first direction falls within a range of 118 to 236 $mm^2$.

17. The apparatus of claim 16, wherein the length of the gas supply cylindrical portion in the first direction falls within a range of 6.5 to 11.5 mm, and the inside area of the first connector in the direction substantially perpendicular to the first direction falls within a range of 140 to 220 $mm^2$.

18. The apparatus of claim 16, wherein the length of the gas supply cylindrical portion in the first direction falls within a range of 7.2 to 10.8 mm, and an inside area of the first connector in the direction substantially perpendicular to the first direction falls within a range of 146 to 210 $mm^2$.

19. The apparatus of claim 15, wherein the gas supply cylindrical portion has a substantially circular cylindrical shape and an inner diameter of 10 to 20 mm, and the gas passing opening has a substantially circular shape and a diameter of 8 to 12.5 mm.

20. The apparatus of claim 19, wherein the inner diameter of the gas supply cylindrical portion falls within a range of 11.5 to 18.5 mm and the diameter of the gas passing opening falls within a range of 8.3 to 12 mm.

21. The apparatus of claim 19, wherein inner diameter of the gas supply cylindrical portion falls within a range of 12.5 to 17.5 mm and the diameter of the gas passing opening falls within a range of 8.6 to 11.6 mm.

22. The apparatus of claim 1, wherein a pair of left and right ventilation holes, corresponding to the positions of the left and right nostrils of the mask wearer when the mask main body is put on the head of said mask wearer, are formed in the mask main body and an opening area of each of the holes falls within a range of 630 to 1,260 $mm^2$.

23. The apparatus of claim 22, wherein the opening area of each of the holes falls within a range of 760 to 1,180 $mm^2$.

24. The apparatus of claim 22, wherein the opening area of each of the holes falls within a range of 790 to 1,140 $mm^2$.

25. The apparatus of claim 13, wherein the apparatus is an oxygen mask apparatus.

26. The apparatus of claim 1, further comprising a gas straightening portion having a substantially inverted frustum shape projecting toward the gas introduction space from the gas introduction opening, wherein:
the first gas introduction opening introduces the first gas to the gas introduction space such that it flows to an inner side of the gas straightening portion; and
the second gas introduction opening introduces the second gas to the gas introduction space such that it flows to an outer side of the gas straightening portion.

27. A gas mask supply connecting apparatus that connects a gas supply tube to a gas mask, the apparatus comprising:
a first connector having a first gas introduction opening through which a first gas exits the first connector and enters the gas mask in a first direction corresponding to the axial direction of the first connector, and a second gas introduction opening through which a second gas exits the first connector and enters the gas mask in a second direction substantially orthogonal to the axial direction of the first connector, such that the second gas surrounds an outer circumference of the first gas in a substantially ring-like shape inside the gas mask.

28. The apparatus of claim 27, further comprising:
a second connector connected to the first connector; and
a third connector connected to the second connector and the gas supply tube.

29. The apparatus of claim 27, wherein the first gas and the second gas are oxygen.

* * * * *